(12) United States Patent
Schindler et al.

(10) Patent No.: US 6,916,756 B2
(45) Date of Patent: Jul. 12, 2005

(54) REGENERATION OF A DEHYDROGENATION CATALYST

(75) Inventors: Goetz-Peter Schindler, Mannheim (DE); Werner Magin, Mannheim (DE); Klaus Harth, Altleiningen (DE)

(73) Assignee: BASF AG, Ludwigshafen (DE)

( * ) Notice: Subject to any disclaimer, the term of this patent is extended or adjusted under 35 U.S.C. 154(b) by 217 days.

(21) Appl. No.: 10/432,998

(22) PCT Filed: Dec. 3, 2001

(86) PCT No.: PCT/EP01/14094

§ 371 (c)(1),
(2), (4) Date: May 29, 2003

(87) PCT Pub. No.: WO02/45852

PCT Pub. Date: Jun. 13, 2002

(65) Prior Publication Data

US 2004/0029715 A1 Feb. 12, 2004

(30) Foreign Application Priority Data

Dec. 4, 2000 (DE) .......................... 100 60 099

(51) Int. Cl.$^7$ .......................... B01J 38/10; B01J 38/12; B01J 38/14; B01J 38/18
(52) U.S. Cl. .......................... 502/38; 502/50; 502/52; 502/53
(58) Field of Search .......................... 502/38, 50, 52, 502/53

(56) References Cited

U.S. PATENT DOCUMENTS

| | | | | |
|---|---|---|---|---|
| 2,671,763 A | * | 3/1954 | Winstrom et al. | 502/50 |
| 3,357,915 A | * | 12/1967 | Young | 208/111.15 |
| 3,360,481 A | * | 12/1967 | McLaren et al. | 502/53 |
| 3,480,558 A | * | 11/1969 | Lum et al. | 502/50 |
| 3,937,660 A | | 2/1976 | Yates et al. | 208/140 |
| 3,986,982 A | * | 10/1976 | Crowson et al. | 502/37 |
| 4,358,395 A | * | 11/1982 | Haag et al. | 502/53 |
| 4,752,595 A | * | 6/1988 | McCullen et al. | 502/50 |
| 4,788,371 A | | 11/1988 | Imai et al. | 585/443 |
| 4,902,849 A | * | 2/1990 | McKay et al. | 585/660 |
| 5,087,792 A | | 2/1992 | Cottrell et al. | 585/661 |
| 5,430,209 A | | 7/1995 | Agaskar et al. | 585/315 |
| 5,733,518 A | | 3/1998 | Durante et al. | 423/248 |
| 5,817,596 A | | 10/1998 | Akporiaye et al. | 502/327 |
| 6,294,492 B1 | * | 9/2001 | Lin | 502/35 |
| 6,309,998 B1 | * | 10/2001 | Bowman et al. | 502/242 |

FOREIGN PATENT DOCUMENTS

| | | | |
|---|---|---|---|
| DE | 1667206 | 8/1969 | |
| DE | 2212204 | 3/1972 | |
| DE | 2439010 | 3/1975 | |
| EP | 382164 B1 * | 7/1994 | ........... C07B/35/04 |
| EP | 806242 | 11/1997 | |
| EP | 838534 | 4/1998 | |
| GB | 1257282 | 12/1971 | |
| WO | 94/29021 | 12/1994 | |
| WO | 96/37299 | 11/1996 | |
| WO | 00/72967 | 12/2000 | |

* cited by examiner

*Primary Examiner*—Stanley S. Silverman
*Assistant Examiner*—Jonas N. Strickland
(74) *Attorney, Agent, or Firm*—Novak Druce & Quigg, LLP

(57) ABSTRACT

A process for regenerating a dehydrogenation catalyst comprises the steps (a)–(f):

(a) flushing with inert gas at a pressure of from 0.5 to 2.0 bar and a gas hourly velocity of from 1000 to 50 000 h$^{-1}$;
(b) passing an oxygen-containing gas mixture comprising an inert gas through the catalyst at a pressure of from 2 to 20 bar and a gas hourly velocity of from 1000 to 50 000 h$^{-1}$ for from 0.25 to 24 hours while increasing the oxygen concentration stepwise or continuously from an initial value of from 0.01 to 1% by volume of $O_2$ to a final value of from 10 to 25% by volume of $O_2$;
(c) optionally passing an oxygen-containing gas mixture comprising an inert gas through the catalyst at a pressure of from 0.5 to 20 bar and a gas hourly velocity of from 10 to 500 h$^{-1}$ for from 0.25 to 100 h, with the oxygen concentration being from 10 to 25% by volume of $O_2$;
(d) optionally changing the pressure repeatedly, rapidly and in opposite directions by a factor of from 2 to 20 within the range from 0.5 to 20 bar;
(e) flushing with an inert gas;
(f) activating the catalyst by means of hydrogen;
where at least one of the steps (c) or (d) is carried out and the entire regeneration process is carried out at from 300 to 800° C.

20 Claims, No Drawings

REGENERATION OF A DEHYDROGENATION CATALYST

The present invention relates to a process for regenerating dehydrogenation catalysts which are used in heterogeneously catalyzed dehydrogenation of dehydrogenatable $C_2$–$C_{30}$-hydrocarbons.

Dehydrogenated hydrocarbons are required in large amounts as starting materials for numerous industrial processes. For example, dehydrogenated hydrocarbons are used in the production of detergents, antiknock gasoline and pharmaceutical products. Likewise, numerous plastics are produced by polymerization of olefins.

Propylene, for example, is used for preparing acrylonitrile, acrylic acid or $C_4$-oxo alcohols. Propylene is at present produced predominantly by steam cracking or by catalytic cracking of suitable hydrocarbons or hydrocarbon mixtures such as naphtha.

U.S. Pat. No. 4,788,371 describes a process for the steam dehydrogenation of dehydrogenatable hydrocarbons in the gas phase in combination with oxidative reheating of the intermediates. In this process, the same catalyst is used for the selective oxidation of hydrogen and the steam dehydrogenation. Hydrogen can be introduced as co-feed. The catalyst used comprises a noble metal of group VIII, an alkali metal and a further metal from the group consisting of B, Ga, In, Ge, Sn and Pb on an inorganic oxide support such as aluminum oxide. The process can be carried out in one or more stages in a fixed or moving bed.

WO 94/29021 describes a catalyst comprising a support consisting essentially of a mixed oxide of magnesium and aluminum Mg(Al)O together with a noble metal of group VIII, preferably platinum, a metal of group IVA, preferably tin, and optionally an alkali metal, preferably cesium. The catalyst is used in the dehydrogenation of hydrocarbons, which can be carried out in the presence of oxygen.

U.S. Pat. No. 5,733,518 describes a process for the selective oxidation of hydrogen by means of oxygen in the presence of hydrocarbons such as n-butane over a catalyst comprising a phosphate of germanium, tin, lead, arsenic, antimony or bismuth, preferably tin. The combustion of the hydrogen generates, in at least one reaction zone, the heat of reaction necessary for the endothermic dehydrogenation.

EP-A 0 838 534 describes a catalyst for the steam-free dehydrogenation of alkanes, in particular isobutane, in the presence of oxygen. The catalyst used comprises a platinum group metal applied to a support comprising tin oxide/zirconium oxide with at least 10% of tin. The oxygen content in the feed stream to the dehydrogenation is matched so that the quantity of heat generated by combustion of hydrogen with oxygen is the same as the quantity of heat required for the dehydrogenation.

WO 96/33151 describes a process for dehydrogenating a $C_2$–$C_5$ alkane in the absence of oxygen over a dehydrogenation catalyst comprising Cr, Mo, Ga, Zn or a group VIII metal with simultaneous oxidation of the resulting hydrogen over a reducible metal oxide such as the oxides of Bi, In, Sb, Zn, Tl, Pb or Te. The dehydrogenation has to be interrupted regularly in order to reoxidize the reduced oxide by means of an oxygen source. U.S. Pat. No. 5,430,209 describes a corresponding process in which the dehydrogenation step and the oxidation step proceed sequentially and the associated catalysts are physically separate from one another. Catalysts used for the selective oxidation of hydrogen are oxides of Bi, Sb and Te and also their mixed oxides.

In heterogeneously catalyzed dehydrogenations of hydrocarbons, small amounts of high-boiling, high molecular weight organic compounds or carbon are generally formed over time and these deposit on the catalyst surface and in the pores and deactivate the catalyst as time goes on. The catalyst sometimes has to be regenerated under drastic conditions and using corrosive gases such as chlorine. The catalysts sometimes can no longer be fully regenerated and therefore has only a short operating life.

The exhausted dehydrogenation catalysts are customarily regenerated by flushing with inert gas, passing an oxygen-containing gas mixture through them, flushing with inert gas and subsequently activating them by means of hydrogen, with atmospheric pressure being employed for the regeneration. In the process described in U.S. Pat. No. 5,087,792, the catalyst is regenerated by flushing with inert gas, passing an oxygen-containing gas mixture through it, flushing with inert gas and subsequently passing an HCl/oxygen mixture through it in order to redisperse the active metal (palladium) on the support.

It is an object of the present invention to provide an effective process for regenerating exhausted dehydrogenation catalysts.

We have found that this object is achieved by a process for regenerating a dehydrogenation catalyst, which comprises the steps (a)–(f):

(a) flushing with inert gas at a pressure of from 0.5 to 2.0 bar and a gas hourly velocity of from 1000 to 50 000 $h^{-1}$;

(b) passing an oxygen-containing gas mixture comprising an inert gas through the catalyst at a pressure of from 2 to 20 bar and a gas hourly velocity of from 1000 to 50 000 $h^{-1}$ for from 0.25 to 24 hours while increasing the oxygen concentration stepwise or continuously from an initial value of from 0.01 to 1% by volume of $O_2$ to a final value of from 10 to 25% by volume of $O_2$;

(c) optionally passing an oxygen-containing gas mixture comprising an inert gas through the catalyst at a pressure of from 0.5 to 20 bar and a gas hourly velocity of from 10 to 500 $h^{-1}$ for from 0.25 to 100 h, with the oxygen concentration being from 10 to 25% by volume of $O_2$;

(d) optionally changing the pressure repeatedly, rapidly and in opposite directions by a factor of from 2 to 20 within the range from 0.5 to 20 bar;

(e) flushing with an inert gas or steam;

(f) activating the catalyst by means of hydrogen;

where at least one of the steps (c) or (d) is carried out and the entire regeneration process is carried out at from 300 to 800° C.

The dehydrogenation catalyst is preferably present as installed in a dehydrogenation reactor. However, it can also be regenerated in a separate regeneration reactor.

In step (a), flushing with inert gas is preferably continued until the flushing gas contains essentially no traces of dehydrogenation product, for example propene, and hydrogen, i.e. traces which can no longer be detected by means of the customary analytical methods, for example by gas chromatography. In general, flushing for from 0.1 to 24 hours at a pressure of from 0.5 to 2.0 bar and a gas hourly velocity of from 1000 to 50 000 $h^{-1}$ is required to achieve this. The pressure is preferably from 1 to 1.5 bar, and the gas hourly velocity is preferably from 2000 to 20 000 $h^{-1}$. The duration of the flushing step is preferably from 0.1 to 6 hours. Nitrogen is generally used as inert gas. The flushing gas can additionally contain steam in amounts of, for example, from 10 to 90% by volume.

In step (b) an oxygen-containing gas mixture is passed through the catalyst bed to burn off the carbon deposits on the surface of the catalyst particles. As oxygen-containing gas mixture, preference is given to using diluted air which may further comprise an inert gas and also steam, for example in amounts of from 10 to 90% by volume. The oxygen content is gradually increased, generally from an initial concentration of 0.01–1% by volume, for example 0.1% by volume, to a final concentration of from 10 to 25% by volume. If the oxygen-containing gas does not contain any steam and air is employed, the final concentration is generally about 21% by weight of oxygen. It is important that this step is carried out at a pressure significantly above the pressure prevailing during the dehydrogenation. The pressure is preferably from 3 to 7 bar, for example 4–6 bar The treatment time is preferably from 0.5 to 12 hours, for example from 1 to 9 hours. In general, a high gas hourly velocity is employed. This is preferably from 2000 to 20000 $h^{-1}$.

In step (c), an oxygen-containing gas mixture having a high oxygen content is passed through the catalyst bed. Preference is given to using air for this purpose. The oxygen-containing gas mixture may comprise steam, for example in amounts of from 10 to 90% by volume. In this step, the carbon deposited in the pores of the catalyst particles is burnt off. This step is carried out at low gas hourly velocities of generally from 10 to 500 $h^{-1}$, preferably from 20 to 100 $h^{-1}$. The pressure is not critical; it can be equal to or lower than the pressure in step (b). In general, it is from 0.5 to 20 bar, preferably from 1 to 5 bar.

In step (d), the pressure is repeatedly changed quickly in opposite directions, so that a pressure increase follows a pressure decrease at short intervals. In this way, the $CO_2$ formed in the pores can be effectively removed. The pressure is preferably changed from 2 to 20 times by a factor of from 2 to 5 within the range from 1 to 5 bar. For example, a total of three pressure increases from 1 to 5 bar and three pressure decreases from 5 to 1 bar are carried out. The total duration of all pressure increase steps and pressure decrease steps is preferably from 0.1 to 1 hour. So that the pressure in the reactor is increased quickly, the gas hourly space velocity chosen should not be too low and is generally from 100 to 50 000 $h^{-1}$, preferably from 1000 to 20 000 $h^{-1}$.

Step (c) and step (d) can be carried out as alternatives; in any case, one of these steps is carried out. Step (d) is carried out especially when step (c) has been carried out over a short period of, for example, from 0.25 to 5 hours. If step (c) has been carried out over a longer period of, for example, from 20 to 100 hours, step (d) can be omitted.

In step (e), the catalyst bed is flushed with inert gas such as nitrogen or argon or steam, preferably for from 1 minute to 1 hour. This is followed in step (f) by the known activation of the catalyst by means of hydrogen. It can be carried out using pure hydrogen or a hydrogen-containing gas which may comprise an inert gas and/or steam, for example in amounts of from 10 to 90% by volume. The activation is preferably carried out at atmospheric pressure over a period of from 10 minutes to 2 hours.

In all steps (a) to (f), the temperature is from 300 to 800° C., preferably from 400 to 700° C.

The process of the present invention can be employed to regenerate any porous catalysts, preferably porous catalysts comprising noble metals on an oxidic support.

Examples are the catalyst which is used in the Linde-Statoil process and comprises Pt and Sn on an $MgO/Al_2O_3$ support, the catalyst which is used in the Star process and comprises Pt on a Zn/Al or Mg/Al spinel and the catalyst which is used in the UOP Oleflex process and comprises Pt on theta-$Al_2O_3$.

The dehydrogenation catalysts which can be regenerated according to the present invention generally comprise a support and an active composition. The support comprises a heat-resistant oxide or mixed oxide. The dehydrogenation catalyst preferably comprises a metal oxide selected from the group consisting of zirconium dioxide, zinc oxide, aluminum oxide, silicon dioxide, titanium dioxide, magnesium oxide, lanthanum oxide, cerium oxide and mixtures thereof as support. Preferred supports are zirconium dioxide and/or silicon dioxide; particular preference is given to mixtures of zirconium dioxide and silicon dioxide.

The active composition of the dehydrogenation catalyst which can be regenerated according to the present invention generally comprises one or more elements of transition group VIII, preferably platinum and/or palladium, particularly preferably platinum. The dehydrogenation catalyst may further comprise one or more elements of main groups I and/or II, preferably potassium and/or cesium. Additionally, the dehydrogenation catalyst may further comprise one or more elements of transition group III including the lanthamides and actinides, preferably lanthanum and/or cerium. Finally, the dehydrogenation catalyst may further comprise one or more elements of main groups III and/or IV, preferably one or more elements from the group consisting of boron, gallium, silicon, germanium, tin and lead, particularly preferably tin.

The dehydrogenation catalyst which can be regenerated according to the present invention preferably comprises at least one element of transition group VIII, at least one element of main groups I and/or II, at least one element of main groups III and/or IV and at least one element of transition group III including the lanthamides and actinides.

The dehydrogenation catalysts which can be regenerated according to the present invention can have been produced as follows:

The dehydrogenation catalysts which can be regenerated according to the present invention can have been produced on the basis of precursors of oxides of zirconium, silicon, aluminum, titanium, magnesium, lanthanum or cerium which can be converted into the oxides by calcination. These can have been produced, for example, by the sol-gel method, precipitation of salts, dehydration of the corresponding acids, dry mixing, slurrying or spray drying. For example, to prepare a $ZrO_2.Al_2O_3.SiO_2$ mixed oxide, a hydrated zirconium oxide of the formula $ZrO_2.xH_2O$ can firstly be prepared by precipitation of a suitable zirconium-containing precursor. Suitable zirconium precursors are, for example, $Zr(NO_3)_4$, $ZrOCl_2$ or $ZrCl_4$. The precipitation itself is carried out by addition of a base such as NaOH, KOH, $Na_2CO_3$ or $NH_3$ and is described, for example, in EP-A 0 849 224.

To prepare a $ZrO_2.SiO_2$ mixed oxide, the previously obtained zirconium-containing precursor can be mixed with a silicon-containing precursor. Well-suited precursors of $SiO_2$ are, for example, water-containing sols of $SiO_2$ such as Ludox™. Mixing of the two components can be carried out, for example, by simple mechanical mixing or by spray drying in a spray dryer.

To prepare a $ZrO_2.SiO_2.Al_2O_3$ mixed oxide, the $SiO_2.ZrO_2$ powder mixture obtained as described above can be admixed with an aluminum-containing precursor. This can be carried out, for example, by simple mechanical mixing in a kneader. However, the $ZrO_2.SiO_2.Al_2O_3$ mixed oxide can also be produced in a single step by dry mixing of the individual precursors.

The powder mixture obtained is admixed with a concentrated acid in a kneader and then converted into a shaped body, e.g. by means of a ram extruder or a screw extruder.

In particular embodiments, the dehydrogenation catalysts which can be regenerated according to the present invention have a defined pore structure. This is influenced in a targeted manner by the use of mixed oxides. Thus, for example, macropores can be generated in the microstructure by the use of $Al_2O_3$ having a low loss on ignition and a defined particle size distribution.

A further possible way of producing supports having specific pore radius distributions for the dehydrogenation catalysts which can be regenerated according to the present invention is addition of various polymers during production of the catalyst; these are partly or completely removed by calcination to form pores in defined pore radius ranges. The polymers and the oxide precursors can be mixed, for example, by simple mechanical mixing or by spray drying in a spray dryer.

Supports having a bimodal pore radius distribution can be produced using PVP (polyvinylpyrrolidone). This is, in one production step, added to one or more oxide precursors of oxides of the elements Zr, Ti, Al or Si, resulting in macropores in the range from 200 to 5000 nm after calcination.

Calcination of the supports for the dehydrogenation catalysts which can be regenerated according to the present invention is advantageously carried out after application of the active components and is carried out at from 400 to 1000° C., preferably from 500 to 700° C., particularly preferably from 550 to 650° C. and in particular from 560 to 620° C.

After calcination, the supports of the dehydrogenation catalysts which can be regenerated according to the present invention generally have high BET surface areas. The BET surface areas are generally greater than 40 $m^2/g$, preferably greater than 50 $m^2/g$, particularly preferably greater than 70 $m^2/g$. The pore volume of the dehydrogenation catalysts which can be regenerated according to the present invention is usually from 0.2 to 0.6 ml/g, preferably from 0.25 to 0.5 ml/g. The mean pore diameter of the dehydrogenation catalysts which can be regenerated according to the present invention, which can be determined by Hg porosimetry, is from 3 to 20 nm, preferably from 4 to 15 nm.

A further characteristic of one embodiment of the dehydrogenation catalysts which can be regenerated according to the present invention is a bimodal pore radius distribution. The pores are in the range up to 20 nm and in the range from 40 to 5000 nm. These pores make up a total of at least 70% of the total pore volume of the dehydrogenation catalyst. The proportion of pores smaller than 20 nm is generally from 20 to 60%, and the proportion of pores in the range from 40 to 5000 nm is generally likewise from 20 to 60%.

The application of the dehydrogenation-active component, usually a metal of transition group VIII, is generally carried out by impregnation with a suitable metal salt precursor. Instead of impregnation, the dehydrogenation-active component can also be applied by other methods such as spraying-on of the metal salt precursor. Suitable metal salt precursors are, for example, the nitrates, acetates and chlorides of the corresponding metals; complex anions of the metals used are also possible. Preference is given to using platinum as $H_2PtCl_6$ or $Pt(NO_3)_2$. Suitable solvents for the metal salt precursors are water and organic solvents. Water and lower alcohols such as methanol and ethanol are particularly useful.

When using noble metals as dehydrogenation-active component, suitable precursors also include the corresponding noble metal sols which can be produced by one of the known methods, for example by reduction of a metal salt by means of a reducing agent in the presence of a stabilizer such as PVP. The technique for producing the sol is described in detail in the German patent application DE 195 00 366.

The amount of noble metal present as dehydrogenation-active component in the dehydrogenation catalysts which can be regenerated according to the present invention is from 0 to 5% by weight, preferably from 0.05 to 1% by weight, particularly preferably from 0.05 to 0.5% by weight.

The further components of the active composition can be applied either during production of the support, for example by coprecipitation, or subsequently, for example by impregnating the support with suitable precursor compounds. Precursor compounds used are generally compounds which can be converted into the corresponding oxides by calcination. Suitable precursor compounds are, for example, hydroxides, carbonates, oxalates, acetates, chlorides or mixed hydroxyl carbonates of the appropriate metals.

In further embodiments of the catalysts which can be regenerated according to the present invention, the active composition comprises the following further components:

at least one element of main group I or II, preferably cesium and/or potassium, in an amount of from 0 to 20% by weight, preferably from 0.1 to 15% by weight, particularly preferably from 0.2 to 10% by weight;

at least one element of transition group III including the lanthamides and actinides, preferably lanthanum and/or cerium in an amount of from 0 to 20% by weight, preferably from 0.1 to 15% by weight, particularly preferably from 0.2 to 10% by weight;

at least one element of main groups III and IV, preferably tin, in an amount of from 0 to 10% by weight.

The dehydrogenation catalyst can be used as a fixed bed in the reactor or, for example, in the form of a fluidized bed and can have an appropriate shape. Suitable shapes are, for example, granules, pellets, monoliths, spheres or extrudates (rods, wagon wheels, stars, rings).

As hydrocarbons to be dehydrogenated, it is possible to use paraffins, alkylaromatics, naphthenes or olefins having from 2 to 30 carbon atoms. The process is particularly useful for the dehydrogenation of straight-chain or branched hydrocarbons having a chain length of from 2 to 15 carbon atoms, preferably from 2 to 5 carbon atoms. Examples are ethane, propane, n-butane, isobutane, n-pentane, isopentane, n-hexane, n-heptane, n-octane, n-nonane, n-decane, n-undecane, n-dodecane, n-tridecane, n-tetradecane, n-pentadecane. The particularly preferred hydrocarbon is propane. In the further description of the invention, reference will frequently be made to this particularly preferred case of propane dehydrogenation, but the corresponding features also apply analogously to other hydrocarbons capable of dehydrogenation.

The catalysts which can be regenerated according to the present invention are used in all customary types of reactors.

The catalysts which can be regenerated according to the present invention can be used in a fixed-bed tube reactor or shell-and-tube reactor. In these, the catalyst (dehydrogenation catalyst and optionally a specific oxidation catalyst) is located as a fixed bed in a reaction tube or in a bundle of reaction tubes.

The catalysts which can be regenerated according to the present invention may be used in a moving bed reactor. The moving catalyst bed can, for example, be accommodated in a radial flow reactor. In this, the catalyst slowly moves from the top downward, while the reaction gas mixture flows radially. This mode of operation is employed, for example, in the UOP Oleflex dehydrogenation process. The dehydrogenation catalyst used there generally has a spherical shape.

The catalysts which can be regenerated according to the present invention can also be used in a fluidized bed. In this case, it is advantageous to operate two fluidized beds in parallel, with one generally undergoing regeneration at a given time.

The catalysts which can be regenerated according to the present invention can be used in a tray reactor. This contains one or more successive catalyst beds. The number of catalyst beds can be from 1 to 20, advantageously from 2 to 8, in particular from 4 to 6. The reaction gas preferably flows radially or axially through the catalyst beds. In general, such a tray reactor is operated using a fixed catalyst bed.

The invention is illustrated by the following examples.

EXAMPLES

Example 1

Catalyst Production

A solution of 59.96 g of $SnCl_2.2H_2O$ and 39.45 g $H_2PtCl_6.6H_2O$ in 1600 ml of ethanol is poured over 5000 g of a $ZrO_2.SiO_2$ mixed oxide in the form of extrudates from Norton (diameter of the extrudates: 3 mm, length of the extrudates: 3 mm).

The composition is rotated at room temperature for 2 h, subsequently dried at 100° C. for 15 hours and calcined at 560° C. for 3 hours. A solution of 38.4 g of $CsNO_3$, 67.7 g of $KNO_3$ and 491.65 g of $La(NO_3)_3$ in 1600 ml of $H_2O$ is then poured over the catalyst. The catalyst is rotated at room temperature for 2 hours, subsequently dried at 100° C. for 15 hours and calcined at 560° C. for 3 hours.

The catalyst has a BET surface area of 84 $m^2/g$, mercury porosimetry measurements indicate a pore volume of 0.26 ml/g, a pore area of 71 $m^2/g$ and a mean pore radius of 11.2 nm. 70% of the pore volume is made up by pores having a diameter of not more than 20 nm, about 20% of the pore volume is made up by pores having a diameter of from 40 to 100 nm and about 30% of the pore volume is made up by pores having a diameter of more than 40 and less than 5000 nm.

Example 2

Regeneration of the Catalyst 1000 ml of the catalyst produced as described in example 1 are diluted with 500 ml of steatite and installed in a tube reactor having an internal diameter of 40 mm. The catalyst is treated in succession, for 30 minutes each at 500° C., firstly with hydrogen, then with diluted air (80% nitrogen and 20% air) and subsequently again with hydrogen. The operations are each separated by 15 minutes of flushing with nitrogen. Subsequently, 500 standard l/h of propane (99.5% pure) and steam in a molar ratio of propane/$H_2O$ of 1:1 are passed over the catalyst at 625° C. The pressure is 1.5 bar, and the gas hourly velocity (GHSV) over the catalyst is 1000 $h^{-1}$. The reaction products are analyzed by gas chromatography. After a reaction time of 2 hours, 47% of the propane used is being converted into propene with a selectivity of 95%. After a reaction time of 12 hours, the conversion is 39% and the selectivity is 95%. The propane feed is turned off and the reactor is flushed with nitrogen and steam (GHSV=2000 $h^{-1}$). Diluted air (98% nitrogen and 2% air) is subsequently passed over the catalyst at 500° C. and a pressure of 4 bar. The air content is subsequently increased three times (firstly to 96% nitrogen and 4% air, then 92% nitrogen and 8% air, then 83% nitrogen and 17% air). The GHSV is always 2000 $h^{-1}$. Subsequently, pure air (GHSV= 500 $h^{-1}$) is passed over the catalyst until the $CO_2$ concentration in the output gas is less than 0.04% by volume. Remaining adsorbed $CO_2$ is desorbed from the catalyst by quickly reducing and restoring the reactor pressure (4 bar→1 bar→4 bar) three times. The reactor is then flushed with nitrogen for 15 minutes and hydrogen is then passed over the catalyst for 30 minutes. Propane is once again introduced as feed. After a dehydrogenation time of 2 hours at 625° C., a 48% conversion of propane is being achieved at a selectivity of 95%. After a dehydrogenation time of 12 hours, the conversion is 39% and the selectivity is 95%. Repeating the same regeneration and dehydrogenation sequence leads to a propane conversion of 47% at a propene selectivity of 95% after 2 hours at 625° C. After a dehydrogenation time of 12 hours, the conversion is 39% and the selectivity is 95%.

Comparative Example

Regeneration of the Catalyst 1000 ml of the catalyst produced as described in Example 1 are diluted with 500 ml of steatite and installed in a tube reactor having an internal diameter of 40 mm. The catalyst is treated in succession, for 30 minutes each at 500° C., firstly with hydrogen, then with diluted air (80% nitrogen and 20% air) and subsequently again with hydrogen. The operations are each separated by 15 minutes of flushing with nitrogen. Subsequently, 500 standard l/h of propane (99.5% pure) and steam in a molar ratio of propane/$H_2O$ of 1:1 are passed over the catalyst at 605° C. The pressure is 1.5 bar, and the gas hourly velocity (GHSV) over the catalyst is 1000 $h^{-1}$. The reaction products are analyzed by gas chromatography. After a reaction time of 2 hours, 45% of the propane used is being converted into propene with a selectivity of 96%. After a dehydrogenation time of 12 hours, the conversion is 35% and the selectivity is 96%. The introduction of propane and of water is subsequently turned off and the reactor is flushed with nitrogen (GHSV=250 $h^{-1}$). Diluted air (92% nitrogen and 8% air) is subsequently passed over the catalyst at 400° C. and 1.5 bar (GHSV=250 $h^{-1}$). The air content is subsequently increased twice (firstly to 83% nitrogen and 17% air, then to 64% nitrogen and 36% air). Pure air is subsequently passed over the catalyst for 3 hours (GHSV=250 $h^{-1}$). The reactor is flushed with nitrogen for 15 minutes and hydrogen is then passed over the catalyst for 30 minutes. Propane and steam are once again introduced as feed. After a dehydrogenation time of 2 hours, at 605° C., 38% conversion of propane is achieved at a selectivity of 96%. After a dehydrogenation time of 12 hours, the conversion was 33% and the selectivity was 96%.

What is claimed is:

1. A process for regenerating a dehydrogenation catalyst, wherein the dehydrogenation catalyst comprises a metal oxide selected from the group consisting of zirconium dioxide, aluminum oxide, silicon dioxide, titanium dioxide, magnesium oxide, lanthanum oxide and cerium oxide, and platinum and/or palladium, which comprises the steps (a)–(f):

(a) flushing with inert gas at a pressure of from 0.5 to 2.0 bar and a gas hourly velocity of from 1000 to 50000 $h^{-1}$;

(b) passing an oxygen-containing gas mixture comprising an inert gas through the catalyst at a pressure of from 2 to 20 bar and a gas hourly velocity of from 1000 to 50 000 $h^{-1}$ for from 0.25 to 24 hours while increasing the oxygen concentration stepwise or continuously from an initial value of from 0.01 to 1% by volume of $O_2$ to a final value of from 10 to 25% by volume of $O_2$;

(c) optionally passing an oxygen-containing gas mixture comprising an inert gas through the catalyst at a pressure of from 0.5 to 20 bar and a gas hourly velocity of from 10 to 500 $h^{-1}$ for from 0.25 to 100 h, with the oxygen concentration being from 10 to 25% by volume of $O_2$;

(d) optionally changing the pressure repeatedly, rapidly and in opposite directions by a factor of from 2 to 20 within the range from 0.5 to 20 bar;

(e) flushing with an inert gas;

(f) activating the catalyst by means of hydrogen;

where at least one of the steps (c) or (d) is carried out and the entire regeneration process is carried out at from 300 to 800° C.

2. A process as claimed in claim 1, wherein the dehydrogenation catalyst to be regenerated is a porous catalyst.

3. A process as claimed in claim 1, wherein the dehydrogenation catalyst comprises zirconium dioxide and/or silicon dioxide.

4. A process as claimed in claim 3, wherein the dehydrogenation catalyst comprises at least one element of main group I or II, at least one element of main group III or IV and at least one element of transition group III including the lanthanides and actinides.

5. A process as claimed in claim 3, wherein the dehydrogenation catalyst comprises cesium and/or potassium.

6. A process as claimed in claim 3, wherein the dehydrogenation catalyst comprises lanthanum and/or cerium.

7. A process as claimed in claim 3, wherein the dehydrogenation catalyst comprises tin.

8. A process as claimed in claim 3, wherein the dehydrogenation catalyst has a bimodal pore radius distribution in which from 70 to 100% of the pore volume is made up by pores having a pore diameter of less than 20 nm or in the range from 40 to 5000 nm.

9. A process as claimed in claim 1, wherein step (a) is carried out over a period of from 0.1 to 24 hours.

10. A process as claimed in claim 1, wherein flushing in step (a) is continued until the flushing gas contains essentially no traces of dehydrogenation product and hydrogen.

11. A process as claimed in claim 1, wherein the gas hourly velocity in step (a) is from 2000 to 20000 $h^{-1}$.

12. A process as claimed in claim 1, wherein the pressure in step (a) is from 1 to 1.5 bar.

13. A process as claimed in claim 1, wherein the oxygen-containing gas mixture used in step (b) is diluted air.

14. A process as claimed in claim 1, wherein the oxygen-containing gas mixture in step (b) contains from 10 to 90% by volume of steam.

15. A process as claimed in claim 1, wherein the pressure in step (b) is from 3 to 7 bar.

16. A process as claimed in claim 1, wherein the oxygen-containing gas mixture used in step (c) is air which may optionally further comprise steam.

17. A process as claimed in claim 1, wherein the gas hourly velocity in step (c) is from 20 to 100 $h^{-1}$.

18. A process as claimed in claim 1, wherein in step (d), the pressure is changed from 2 to 20 times by a factor of from 2 to 5 in the range from 1 to 5 bar.

19. A process as claimed in claim 1, wherein step (c) is carried out over a period of from 0.25 to 5 hours and step (d) is carried out.

20. A process as claimed in claim 1, wherein step (c) is carried out over a period of from 20 to 100 hours and step (d) is not carried out.

* * * * *